(12) United States Patent
Mutti et al.

(10) Patent No.: US 6,759,555 B2
(45) Date of Patent: Jul. 6, 2004

(54) PROCESS FOR THE PREPARATION OF COMBRETASTATINS

(75) Inventors: Stéphane Mutti, Le Perreux sur Marne (FR); Michel Lavigne, Chilly Mazarin (FR); Irina Malejonock, Vitry sur Seine (FR); Jean-Paul Casimir, Eaubonne (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 10/410,547

(22) Filed: Apr. 9, 2003

(65) Prior Publication Data

US 2003/0220404 A1 Nov. 27, 2003

Related U.S. Application Data

(60) Provisional application No. 60/381,333, filed on May 20, 2002.

(30) Foreign Application Priority Data

Apr. 11, 2002 (FR) .............................. 0204499

(51) Int. Cl.[7] ...................... A61K 31/135; C07C 215/56
(52) U.S. Cl. ....................... 564/193; 564/418; 564/443; 548/215
(58) Field of Search ................................. 564/193, 418, 564/443; 548/215

(56) References Cited

U.S. PATENT DOCUMENTS

| | | | |
|---|---|---|---|
| 4,996,237 A | 2/1991 | Pettit et al. | |
| 5,525,632 A | 6/1996 | Ohsumi et al. | |
| 5,674,906 A | 10/1997 | Hatanaka et al. | |
| 5,731,353 A | 3/1998 | Ohsumi et al. | |
| 6,162,930 A | * 12/2000 | Pinney et al. | ................ 549/57 |

OTHER PUBLICATIONS

Database CAPLUS on STN, Acc. No. 2000:373651, Ohsumi et al., Anti–Cancer Drug Design (1999), 14(6), p. 539–548 (abstract).*
Novel combretastatin analogues effective against murine solid tumors: design structure–activity relationships, Ohsumi et al., J. Med. Chem. (1998) 41(16), p. 3022–3032.*
Potential photoaffinity labels for tubulin. Synthesis and evaluation of diazocyclohexadienone and azide analogs of colchicine, combretastatin and 3,4,5–trimethyoxybiphenyl, Olszewski et al., J. Org. Chem. (1994), 59, p. 4285–4296.*
Pinney K G et al., Synthesis and Biological Evaluation of Aryl Azide Derivatives of Combretastatin A–4 as Molecular Probes for Tubulin, Bioorganic & Medicinal Chemistry, 2000, vol. 8, Issue 10, pp 2417–2425.

* cited by examiner

Primary Examiner—Brian Davis
(74) Attorney, Agent, or Firm—Lawrence Martin

(57) ABSTRACT

The present invention provides novel processes for the preparation of combretastatins or stilbene compounds of formulae (I) and (III)

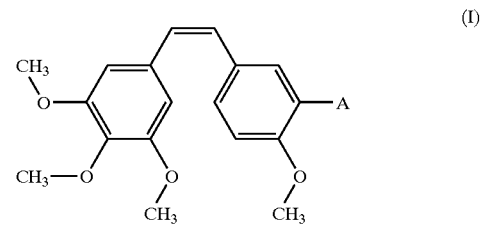

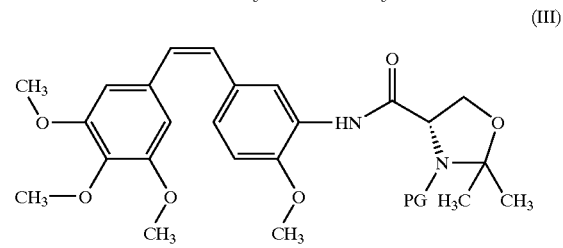

wherein A is NH$_2$ or

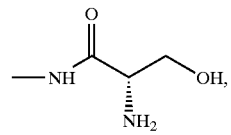

and PG is a protecting group.

The disclosed and claimed processes include (1) Wittig condensation between a nitromethoxybenzaldehyde and a trimethoxybenzylphosphonium salt or between a trimethoxybenzaldehyde and a nitromethoxybenzylphosphonium salt to provide an intermediate compound of formula (I) wherein A is NO$_2$, and subsequent iron powder reduction to provide a compound of formula (I) wherein A is NH$_2$; (2) Wittig condensation of the same precursor aldehydes and phosphonium salts wherein NO$_2$ is replaced by NH$_2$ to provide a compound of formula (I) wherein A is NH$_2$; and (3) a process for condensation of a compound of formula (I) wherein A is NH$_2$ with a doubly protected serinamide to provide an intermediate of formula (III), and subsequent hydrolysis to provide a compound of formula (I) wherein A is —NH—C(=O)CH(NH$_2$)CH$_2$OH, or the pharmaceutically acceptable salts thereof. Also claimed is a compound of formula (III).

20 Claims, No Drawings

PROCESS FOR THE PREPARATION OF COMBRETASTATINS

This application claims priority from French patent application number 0204499, filed Apr. 11, 2002, and the benefit of U.S. Provisional Application No. 60/381,333, filed May 20, 2002.

BACKGROUND OF THE INVENTION

1. Field of the Invention

The present invention relates to a novel process for the preparation of combretastatins and of their derivatives.

2. Description of the Art

The term "combretastatins" or "stilbene derivatives" is understood to mean the derivatives of following general formula (I):

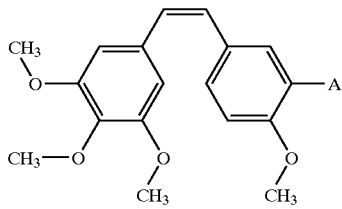

(I)

in which A represents a hydroxyl group or an amino group, and their pharmaceutically acceptable salts.

Mention may be made, among the salts, of the hydrochloride, acetate, phosphate or methanesulphonate. When A in the compound is an amino group, it can also be coupled to amino acids to result in amides, and their pharmaceutically acceptable salts.

The synthesis of stilbene derivatives or combretastatins, which can be in the form of a pharmaceutically acceptable salt, and the pharmaceutical compositions which comprise them are disclosed in U.S. Pat. Nos. 4,996,237, 5,525,632, 5,731,353 and 5,674,906. These patents disclose combretastatins and their metabolites and disclose their in vitro oncologic activity.

According to these patents, combretastatins are prepared from (3,4,5-trimethoxybenzyl)triphenylphosphonium salts, which are condensed with a 3-nitro- or 3-hydroxy-4-methoxybenzaldehyde (the hydroxyl group of which is protected) in the presence of sodium hydride or of lithium derivatives, and then the derivative obtained, when it is nitrated, is reduced in the presence of zinc.

The isomer with the cis configuration is subsequently prepared by the action of light or by chromatographic separation of the mixture.

SUMMARY OF THE INVENTION

The present invention provides novel processes for the preparation of combretastatins or stilbene compounds of formulae (I) and (III)

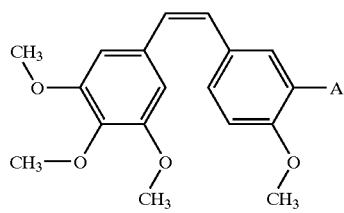

(I)

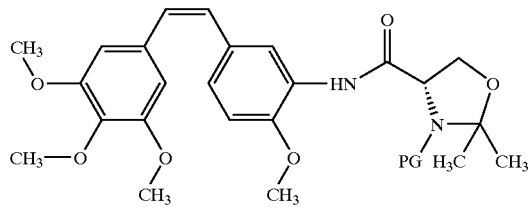

(III)

wherein A is

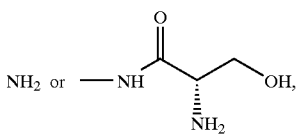

and

PG is a protecting group selected from the group consisting of tert-butoxycarbonyl, benzyloxycarbonyl and 9-fluorenylmethyloxycarbonyl, or the pharmaceutically acceptable salts thereof. In addition, the novel intermediate compound of formula III is disclosed and claimed.

DETAILED DESCRIPTION OF THE INVENTION

A first process route V0 1 for the preparation of derivatives of formula (I) for which A represents an amino group has first been discovered, which process is an improvement to the process disclosed in the abovementioned patents, which consists, after the Wittig condensation of (3,4,5-trimethoxybenzyl)triphenylphosphonium bromide or chloride and 3-nitro-4-methoxybenzaldehyde, in carrying out reduction of the nitro group with of iron, instead of the zinc as is used in the prior publications, which makes it possible to achieve an overall reaction yield, with respect to the aldehyde charged, of 60% (the yield with respect to the aldehyde charged in U.S. Pat. No. 5,525,632 is between 21% and 33%).

The first process route V0 2 consists in condensing 3,4,5-trimethoxybenzaldehyde with (4-methoxy-3-nitrobenzyl)triphenylphosphonium bromide or chloride. For both these first two processes routes V0 1 and V0 2, the reaction is carried out in the presence of a base chosen in particular from potassium tert-butoxide, sodium tert-pentoxide, sodium hydride, butyllithium, LDA (lithium diisopropylamide), sodium methoxide, potassium carbonate or alkaline derivatives of hexamethyldisilazane.

This reaction is carried out in various solvents, such as ethers (THF), polar aprotic solvents (acetonitrile, NMP, DMF, DMSO, and the like), alcohols, aromatic solvents or water, at a temperature which will be adjusted by a person skilled in the art to the base used and to the solvent used.

This reaction, as regards the first process route V0 2, is described in particular in the publication by K. G. Piney which appeared in Bioorg. Med. Chem., 8(2000), 2417–2425.

2-Methoxy-5-[2-(3,4,5-trimethoxyphenyl)vinyl] nitrobenzene is reduced according to the improved process of the invention by the action of iron. It is advantageous to use an amount of iron in excess if complete conversion of the starting material is desired. This excess is advantageously greater than 2 equivalents per one mol of starting nitro derivative.

It has been shown that the same stage, carried out in the presence of zinc in acetic acid, a conventional solvent for reductions with zinc, does not make it possible to obtain complete reaction (in U.S. Pat. No. 5,525,632, the yield of the reduction carried out on the pure Z isomer varies between 46% and 66%) and, moreover, that the amounts of zinc used are large and consequently result in considerable industrial waste. Furthermore, the process generates a large amount of "azo" compound resulting from coupling between the amino formed and the nitroso intermediate in the reduction.

Reduction with nascent hydrogen, generated by ammonium formate in the presence of a conventional catalyst, such as palladium or platinum, leads to high isomerization of the double bond to the undesirable E isomer and to partial saturation of the double bond.

The abovementioned Piney publication describes the reduction by sodium hydrosulphite of a pure nitro Z isomer, obtained after chromatography and recrystallization, leading to an amino Z isomer with a yield of only 37%.

Hydrogenations with molecular hydrogen, catalysed by platinum or palladium, are rarely complete and result in particular in the saturation of the ethylenic double bond.

A second process has also been found which avoids the intermediate reduction stage necessary when starting from a nitro derivative. This is because it is much more economical to condense, according to a first method of carrying out this second process, a (3,4,5-trimethoxybenzyl) triphenylphosphonium bromide or chloride with 3-amino-4-methoxybenzaldehyde or, according to a second method of carrying out this second process, condensing 3,4,5-trimethoxybenzaldehyde with a (3-amino-4-methoxybenzyl)triphenyl-phosphonium salt.

This second process according to its two alternative forms requires a stage in which less in the way of CMR (Cancerogenic, Mutagenic or Reproductive) toxic products are given off in comparison with the first processes routes V0 1 and V0 2, which is a considerable advantage at the industrial level from the viewpoint of safety and production cost.

According to the second process route V0 3 for implementing the invention, the (3,4,5-trimethoxybenzyl) triphenylphosphonium salt and 3-amino-4-methoxybenzaldehyde are brought together and the reaction is carried out, preferably, in the presence of a base chosen in particular from potassium tert-butoxide, sodium tert-pentoxide, sodium hydride, butyllithium, LDA, sodium methoxide, potassium carbonate or alkaline derivatives of hexamethyldisilazane. Use is preferably made of sodium methoxide.

This reaction is carried out in various solvents, such as ethers (THF), polar aprotic solvents (acetonitrile, NMP, DMF, DMSO, and the like), alcohols, aromatic solvents or water, at a temperature which will be adjusted by a person skilled in the art to the base used and to the solvent used.

The reaction temperature will be adjusted by a person skilled in the art as to the base used. When methoxide is used, the reaction temperature is preferably between 0° C. and 10° C. After reaction, the base used is neutralized with an acid in aqueous solution, the organic phase is washed and concentrated, and the expected product is obtained after chromatographing the crude concentrate.

According to the second process route V0 4 for implementing the invention, in which the (3-amino-4-methoxybenzyl)triphenylphosphonium salt and 3,4,5-trimethoxybenzaldehyde are brought together, the reaction is preferably carried out in the presence of a base chosen in particular from potassium tert-butoxide, sodium tert-pentoxide, sodium hydride, butyllithium, LDA, sodium methoxide, potassium carbonate or alkaline derivatives of hexamethyldisilazane. Use is preferably made of sodium methoxide.

This reaction is carried out in various solvents, such as ethers (THF), polar aprotic solvents (acetonitrile, NMP, DMF, DMSO, and the like), alcohols, aromatic solvents or water, at a temperature which will be adjusted by a person skilled in the art to the base used and to the solvent used.

The reaction temperature will be adjusted by a person skilled in the art to the base used. When methoxide is used, the reaction temperature is preferably between 0° C. and 10° C. After reaction, the base used is neutralized with an acid in aqueous solution, the organic phase is washed and concentrated, and the expected product is obtained after chromatographing the crude concentrate.

The derivative obtained according to the second process route V0 3 or V0 4 or during the second stage of the first process route V0 1 or V0 2 has the formula (IIa):

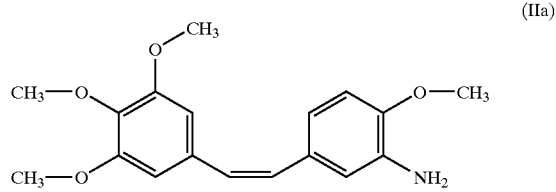

(IIa)

It is advantageous, when it is desired to couple serine with the compound of formula (IIa), to use L-serine doubly protected on the nitrogen of the serine and on the hydroxyl functional group of general formula (IIb)

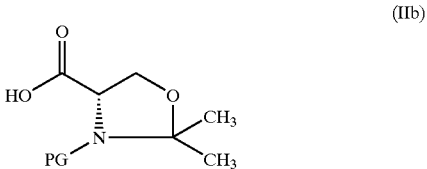

(IIb)

where PG represents a protective group for the amine functional group well known to a person skilled in the art, to give a novel intermediate of following general formula (III):

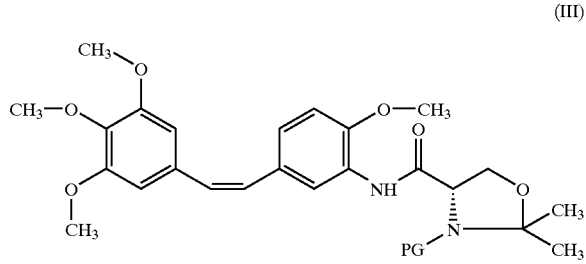

(III)

which is subsequently cleaved, preferably simultaneously with the opening of the ring, by acid hydrolysis according to a deprotection reaction well known to a person skilled in the art. Preferably, the PG group of the formulae (IIb) or (III) represents a protective group selected from the following groups: tert-butoxycarbonyl, benzyloxycarbonyl (CBZ) or 9-fluorenylmethyloxycarbonyl (FMOC).

The compound of formula (III) above is novel and is claimed as such.

The condensation is advantageously carried out in the presence of EDCI (1-(3-dimethylaminopropyl)-3-ethylcarbodiimide hydrochloride) or in the presence of DCC (dicyclohexylcarbodiimide) and of HOBT (hydroxybenzotriazole) or in the presence of DCC (dicyclohexylcarbodiimide) and of HOSU (N-hydroxysuccinimide) or, finally, in the presence of TOTU (O-[(ethoxycarbonyl)cyanomethyleneamino]-N,N,N',N'-tetramethyluronium tetrafluoroborate) or of HBTU (O-benzotriazol-1-yl-N,N,N',N'-tetramethyluronium hexafluorophosphate) or of N,N-carbonyldiimidazole. The reaction is preferably carried out in a solvent which is inert with respect to the reaction, which solvent is chosen in particular from polar aprotic solvents, such as acetonitrile, dimethylformamide, tetrahydrofuran or chlorinated aliphatic solvents, such as dichloromethane, or, finally, esters.

The coupling to the derivative of formula (IIa) can also be carried out by the action of a mixed anhydride, synthesized in situ between a chloroformate or a carboxylic acid chloride, for example pivaloyl chloride, and doubly protected L-serine of formula (IIb), in the presence of a tertiary base of the NMM (N-methylmorpholine) type in various solvents which are inert with respect to the reaction such as, for exampe, esters, ethers, chlorinated solvents, acetonitrile, and the like. The mixed anhydride is preferably prepared at a temperature of between 0° C. and 10° C. and then the reaction is carried out at ambient temperature. After reaction, the reaction mixture is hydrolysed with an aqueous solution, then the phases are separated and the organic phase is washed with aqueous base.

The double deprotection of the compound of formula (III) is carried out by the action of an organic or inorganic acid. Use is preferably made of concentrated aqueous hydrochloric acid in an alcoholic medium. The reaction temperature is, according to a better means of implementation of the invention, preferably between 50° C. and 70° C.

The invention will be more fully described with the help of the following examples, which must not be regarded as limiting the invention.

The composition of the mixtures, the monitoring and the progression of the reactions, and the yield of the unisolated products/intermediates and their assays are determined by HPLC (High Performance Liquid Chromatography) analysis. HPLC conditions: column—octadecyl silicagel; detection—UV 242 nm; mobile phase—water, trifluoroacetic acid, acetonitrile. Thin layer chromatographic analysis (TLC) was performed using silica gel plates with cyclohexane/ethyl acetate.

EXPERIMENTAL

EXAMPLE 1

First Process Route V0 2 According to the Invention (Z)-N-[2-Methoxy-5-[2-(3,4,5-trimethoxyphenyl)vinyl]phenyl]-L-serinamide hydrochloride General Scheme of the Synthesis The novel "inverse Wittig" process, starting from (4-methoxy-3-nitrobenzyl)triphenylphosphonium bromide and 3,4,5-trimethoxybenzaldehyde, makes it possible to obtain the mixture of Z and E isomers of 2-methoxy-5-[2-(3,4,5-trimethoxyphenyl)vinyl]nitrobenzene with a Z/E ratio of 75/25.

This ratio is sufficiently high in the Z nitro isomer to be able to use the Z/E mixture directly in the reduction and to obtain, by crystallization of the hydrochloride, the Z amino isomer with an IS HPLC assay of 97% (IS, internal standardization).

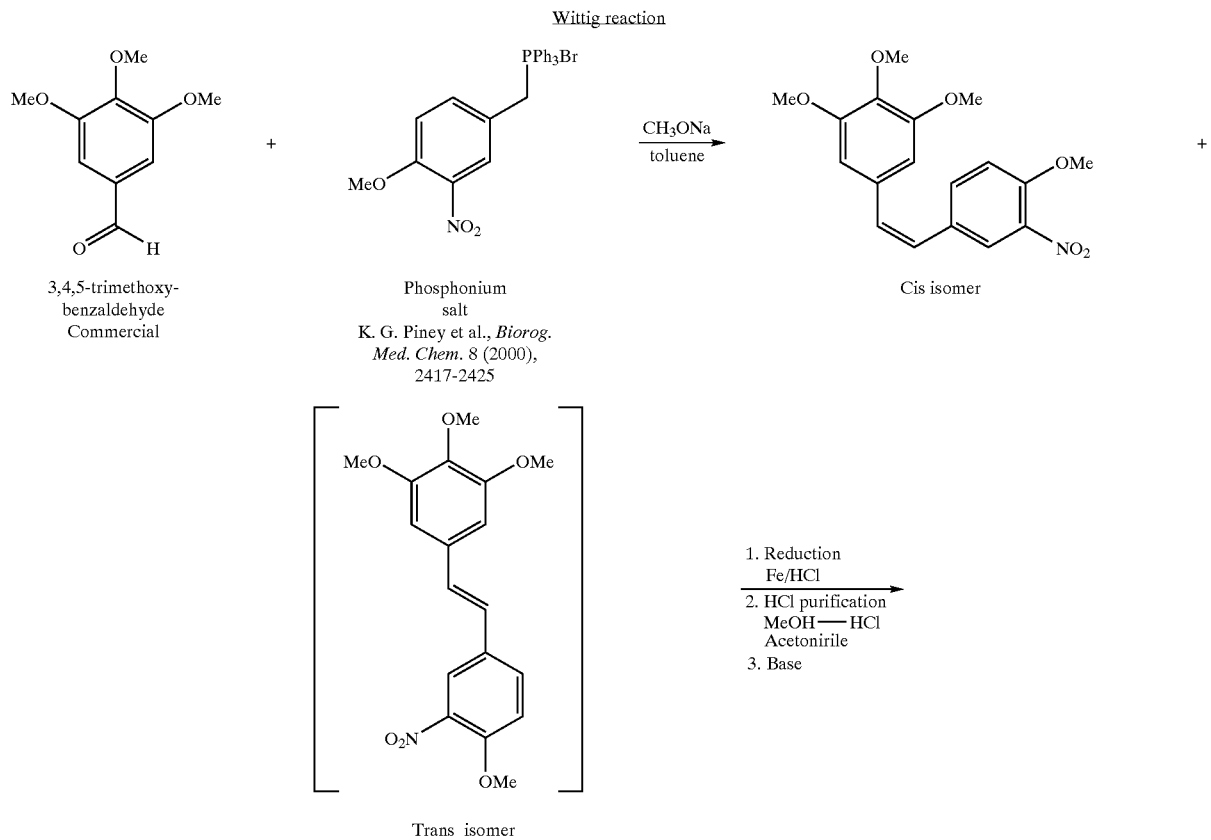

-continued

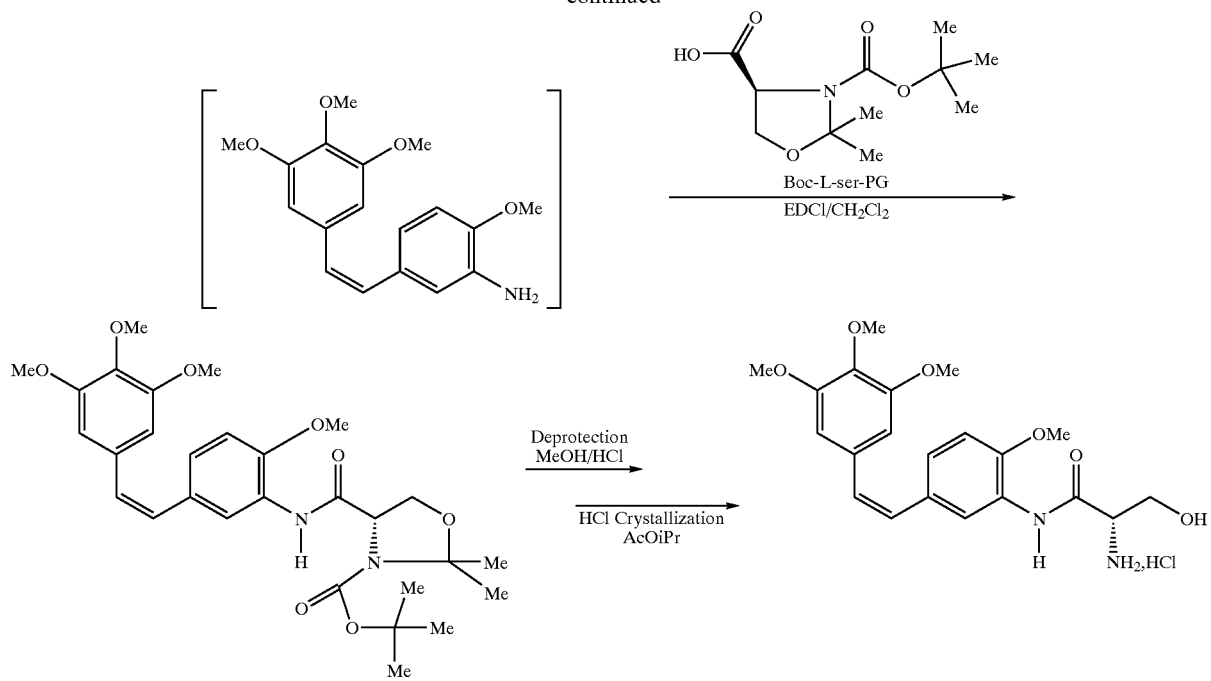

(4-Methoxy-3-nitrobenzyl)triphenylphosphonium bromide (4) is prepared according to the following example

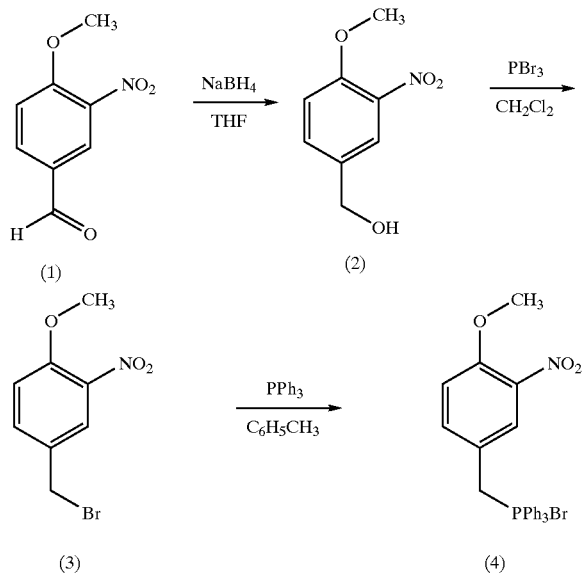

3-4-methoxybenzyl alchol (2)

3-Nitro-4-methoxybenzaldehyde (1, 90.5 g) is charged, followed by 450 ml of THF and 90 ml of ethanol, into a 2-litre three-necked flask equipped with a mechanical stirrer, a thermometer, a T piece, a funnel for the addition of solid and a reflux condenser surmounted by a bubble counter. The resultant pale-yellow solution is cooled to 10° C. and then 10 g of sodium borohydride are charged over 40 minutes at 10–15° C. (the reaction is very exothermic and the temperature has to be maintained with an ice/acetone bath); at the end of the addition, the brown solution turns navy blue. The solution is stirred for 30 minutes at 10° C., the end of the reaction is monitored by TLC (thin layer chromatography), the solution is stirred for an additional 1 hour at 10° C. and then the temperature is allowed to return to ambient temperature.

The addition funnel is replaced by a 500 ml pressure-equalizing dropping funnel, via which 300 ml of distilled water is added dropwise over 30 minutes while maintaining the mixture at 20° C. Gas evolution is observed when the addition of water is started. The mixture is concentrated to $2/3$ volume on a rotary evaporator (50° C./20 mmHg) and a white product crystallizes in the aqueous concentrate in the form of lumps. The cooled aqueous phase is extracted with 250 ml and then 150 ml of dichloromethane, and the combined organic phases are washed with 250 ml of distilled water and then dried over magnesium sulphate. After filtration, the dichloromethane solution is used as is in the following bromination reaction. The yield at this stage is regarded as being 100%. The alcohol (2) is commercially available but very difficult to obtain.

3-Nitro-4-methoxybenzyl bromide (3)

The dichloromethane solution of 3-nitro-4-methoxybenzyl alcohol (2) is charged into a 1 litre three-necked flask equipped with a mechanical stirrer, a thermometer, a T piece, a dropping funnel and a reflux condenser surmounted by a bubble counter, and 100 ml of dichloromethane are added. The stirred solution is cooled to 5° C. and then 135.4 g of phosphorus tribromide are added dropwise while maintaining the temperature at 5° C. The solution is stirred at 5° C. for 1.5 hours, the end of the reaction is monitored by TLC and then 250 ml of saturated sodium hydrogen carbonate solution are added dropwise while maintaining the temperature at 15° C. Very strong evolution of gas takes place with a slight delay as the phosphorus tribromide is added. The organic phase is separated, and is washed successively with 250 ml of distilled water and 200 ml of saturated sodium hydrogen carbonate solution. The organic phase is dried over magnesium sulphate, filtered and concentrated on a rotary evaporator (50° C./20 mmHg). A solid (119 g) in the form of green-yellow felt-like needles is obtained with a chemical yield over two stages of 97%. Product (3) can also be prepared according to the following scheme, described in the publication: K. G. Piney et al., Bioorg. Med. Chem., 8 (2000), 2417–2425.

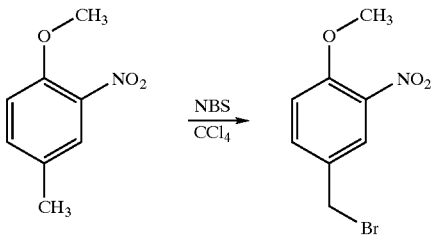

(3-Nitro-4-methoxybenzyl)triphenylphosphonium bromide (4)

3-Nitro-4-methoxybenzyl bromide (3, 119 g) is charged into 1000 ml of stirred toluene in a 2 litre three-necked flask equipped with a mechanical stirrer, a thermometer, a T piece, a funnel for the addition of solids and a reflux condenser surmounted by a bubble counter, and the stirred mixture, warmed to 25° C., forms a solution. Triphenylphosphine (126.5 g) is then added and the resultant solution is gradually heated to 60° C.; a precipitate begins to form at about 30° C. The mixture is maintained at 60–65° C. for 4 hours, is then cooled to 30° C. and is filtered through a sintered glass filter. The filter cake is washed on the filter twice with 300 ml portions of toluene, sucked dry and dried in an oven (35° C./20 mmHg/ hours). (4-Methoxy-3-nitrobenzyl) triphenylphosphonium bromide (217 g) is obtained with a chemical yield of 88%. The synthesis is also described in the publication: (solvent used: dichloromethane) K. G. Piney et al., Bioorg. Med. Chem., 8(2000), 2417–2425.

$^1$H N.M.R. spectrum: (300 MHz, $(CD_3)_2SO$, δ in ppm): 3.90 (s, 3H), 5.26 (d, J=15 Hz, 2H), 7.33 (mt, 2H), 7.41 (mt, 1H), from 7.65 to 8.05 (mt, 15H).

| Mass spectrum: m = 428 | | | |
|---|---|---|---|
| EI | m/z = 262 | $[PPh_3]^+$ | base peak |
| DCI | m/z = 445 | $MNH_4^+$ | |
| | m/z = 428 | $M^+$ | |
| | m/z = 263 | $[PPh_3H]^+$ | base peak |

IR spectrum: (KBr)

2869, 2843, 2776, 1619, 1527, 1438, 1362, 1287, 1270, 1111, 752, 692 and 502 cm$^{-1}$ Z and E Mixture of 2-methoxy-5-[2-(3,4,5-trimethoxyphenyl)vinyl]nitrobenzene (6) and (7)

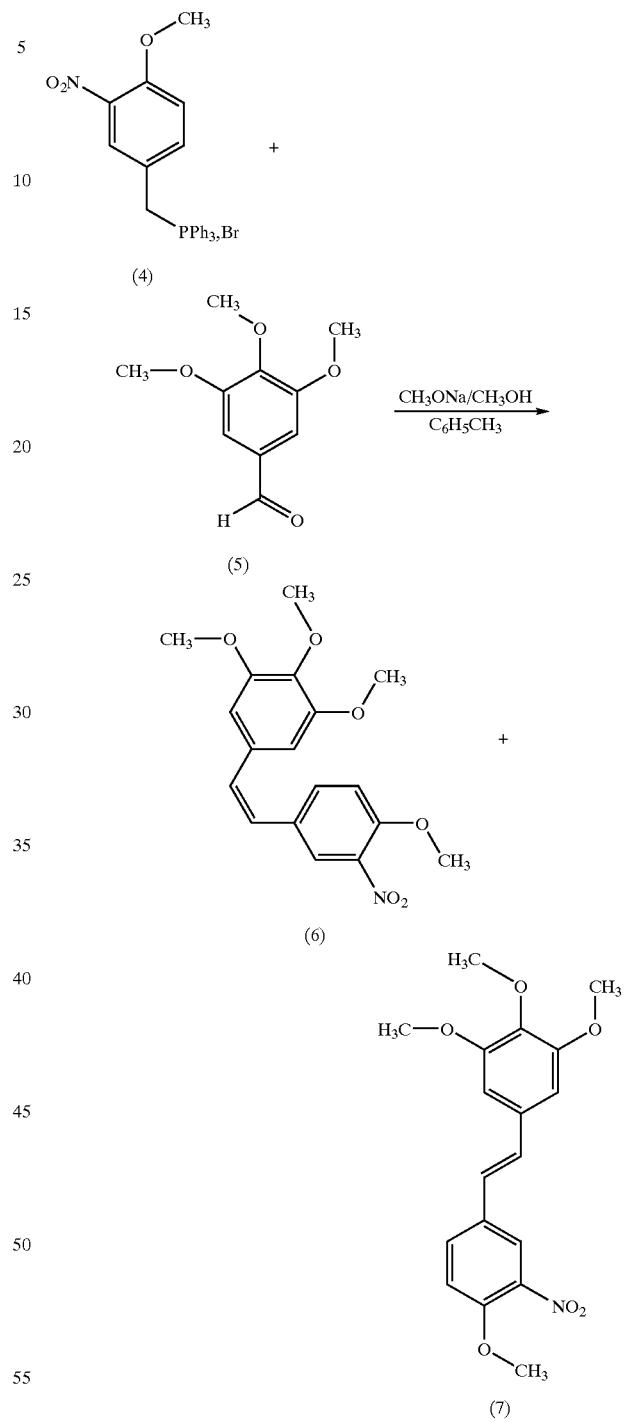

3,4,5-Trimethoxybenzaldehyde (5, 54.7 g), (4-methoxy-3-nitrobenzyl)triphenylphosphonium bromide (4, 148.6 g) and 1300 ml of toluene are charged, at 20° C. and under nitrogen, into a 2 litre three-necked flask equipped with a mechanical stirrer, a thermometer, a T piece, a dropping funnel and a reflux condenser surmounted by a bubble counter. The stirred suspension is cooled to 5° C. using an ice bath and then 63.2 g of a 25% w/w solution of sodium methoxide in methanol are added at 5° C. over 40 minutes. As the addition progresses, the suspension color changes from off-white to yellow and then to brown. The mixture is stirred for 1 hour at 5° C. and the end of the reaction is monitored by HPLC (complete consumption of the aldehyde). Acetic acid (3 g, 0.05 mol) is then added. The suspension is heated to 40° C. and is maintained at 40° C. for 30 minutes. At this temperature, only the salts remain insoluble. The mixture is filtered at 40° C. through a sintered glass filter (No. 3) and the salts are washed on the filter 3 times with 100 ml portions of toluene. The filtrate is returned to a round-bottomed flask with 250 ml of distilled water, and the two-phase mixture is stirred for 20 minutes at 40° C. and then the phases are separated. The toluene phase is washed twice with 250 ml portions of distilled water and then concentrated to dryness on a rotary evaporator. The residue is taken up in 600 ml of isopropanol and 12 ml of toluene at 40° C. The expected product begins to crystallize and the temperature is allowed to return to ambient temperature overnight with slow stirring. The stirred suspension is cooled to and maintained for 1 hour at 5° C., then filtered through a sintered glass filter, and the filter cake is washed twice with 125 ml portions of isopropanol, sucked dry and dried in an oven under vacuum (35° C./30 mmHg/18 hours). A mixture of Z and E isomers (6) and (7) (91.7 g) is obtained with a Z/E ratio of 75/25 (IS IPLC) and a yield of 95%.

The synthesis is also described in the publication: (solvent used: dichloromethane: base used: NaH) K. G. Piney et al., Bioorg. Med. Chem., 8(2000), 2417–2425.

Numerous operating conditions were experimented with, such as:

Solvents: TUF, acetonitrile, methanol and other alcohols, dichloromethane, NMP, DMF, DMSO, and the like.
Bases: potassium t-butoxide, sodium t-pentoxide, sodium hydroxide, NaH, BuLi/LDA, potassium carbonate and the like.
Temperatures: from −10° C. to the reflux temperatures of some solvents.

Z-2-Methoxy-5-[2-(3,4,5-trimethoxyphenyl)vinyl] phenylamine hydrochloride (8):

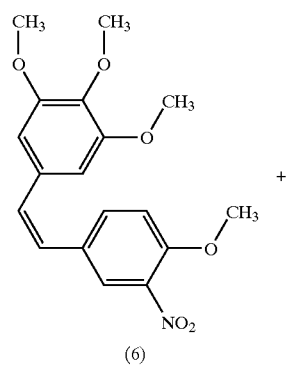

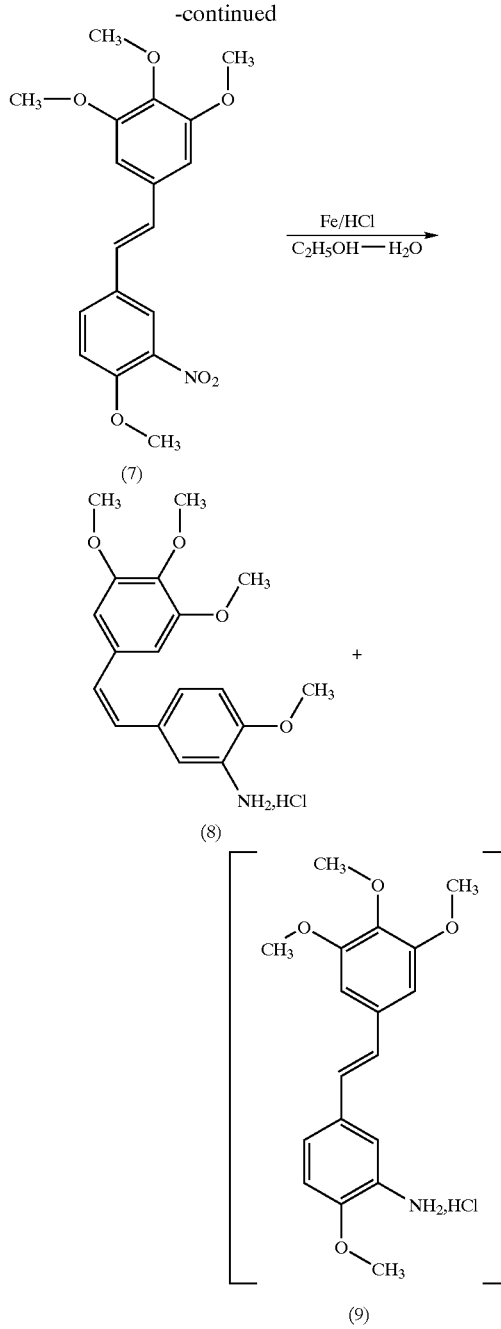

A 75/25 Z and E mixture of 2-methoxy-5-[2-(3,4,5-trimethoxyphenyl)vinyl]-nitrobenzene (6) and (7) (80 g), 640 ml of absolute ethanol and 160 ml of distilled water are charged, at 20° C. and under nitrogen, into a 2 litre three-necked flask equipped with a mechanical stirrer, a thermometer, a T piece, a funnel for the addition of solid, a reflux condenser surmounted by a bubble counter, and a heating bath. The mixture is rapidly stirred and heated in an oil bath, 7.8 ml of 6N hydrochloric acid are added to the suspension at 50° C. and then the temperature of the mixture is raised to 77±2° C. to afford an almost complete solution. Iron powder (52 g) is added portionwise over 5 minutes.

With the first addition, the mixture passes into solution and then a blackish deposit is formed on the walls of the round-bottom flask. The mixture is maintained at 77±2° C. for 2 hours and the disappearance of the starting nitro compounds (6) and (7) is monitored by HPLC. The mixture is allowed to cool to 40° C. and is filtered through a sintered glass filter covered with clarcel (CELITE) and the filter cake is rinsed twice with 160 ml portions of 80/20 ethanol/water mixture. The combined filtrate, aqueous mother liquors and aqueous wash liquors are concentrated on a rotary evaporator. As soon as the azeotrope has been driven off, an oil begins to separate from the residual aqueous phase. The aqueous phase is extracted in a separating funnel twice with 300 ml portions of dichloromethane, and then the combined organic phase is washed twice with 300 ml portions of half-saturated aqueous sodium chloride solution and with 300 ml of distilled water. The organic phase is concentrated to dryness on a rotary evaporator to afford 76 g of an oil which exhibits a Z/E ratio of 80/20 by HPLC. This oil is dissolved in 591 ml of methanol and transferred into a stirred 1 litre round-bottom flask, 100 ml of 2.32N methanolic hydrochloric acid are then added, precipitation is initiated and the mixture is allowed to precipitate overnight with stirring. The amount of methanol and methanolic hydrochloric acid is such that the final concentration of Z isomer (determined by HPLC) is equal to 8.8% w/v. In the morning, the mixture is filtered through a sintered glass filter. The dried filter cake weighs 8.2 g and is composed only of the E isomer (HPLC). The filtrate (693 g), ratio Z/E=86/14 (IS HPLC), is concentrated to half weight on a rotary evaporator, 400 ml of acetonitrile are added to the 347 g of concentrate and the mixture is reconcentrated until a concentrate of 347 g is again obtained. Acetonitrile (1000 ml) is then added and the mixture is concentrated until crystallization begins. The concentrate is then transferred into a stirred 4 litre round-bottom flask containing 1500 ml of acetonitrile at 60° C. The mixture copiously precipitates. The mixture is kept stirred at 60° C. for 2.5 hours and is allowed to cool to 30° C. over approximately 1 hour. The slurry is filtered through a sintered glass filter (the E isomer (9) is soluble in the filtrate). The filter cake is washed twice with 200 ml portions of acetonitrile and dried in an oven (35° C./30 mmHg/18 hours). Z-2-methoxy-5-[2-(3,4,5-trimethoxyphenyl)vinyl]-phenylamine hydrochloride(45.7 g, 8) is obtained with an IS HPLC assay of 97% and a yield as such of 56%, i.e., a yield of Z isomer obtained with respect to Z isomer charged of 72%.

EXAMPLE 2

Synthesis According to the Second Process Route V0 3 According to the Invention.

The advantage of the second process route V0 3 with respect to the first "inverse Wittig" process route V0 2 is that of carrying out the Wittig reaction between a product which has already been reduced, the aminoaldehyde (1a), and the phosphonium (2a) and thus of eliminating a chemical stage which gives off CMR products.

(Z)-N-[2-Methoxy-5-[2-(3,4,5-trimethoxyphenyl)vinyl]phenyl]-L-serinamide hydrochloride General Scheme of the Synthesis

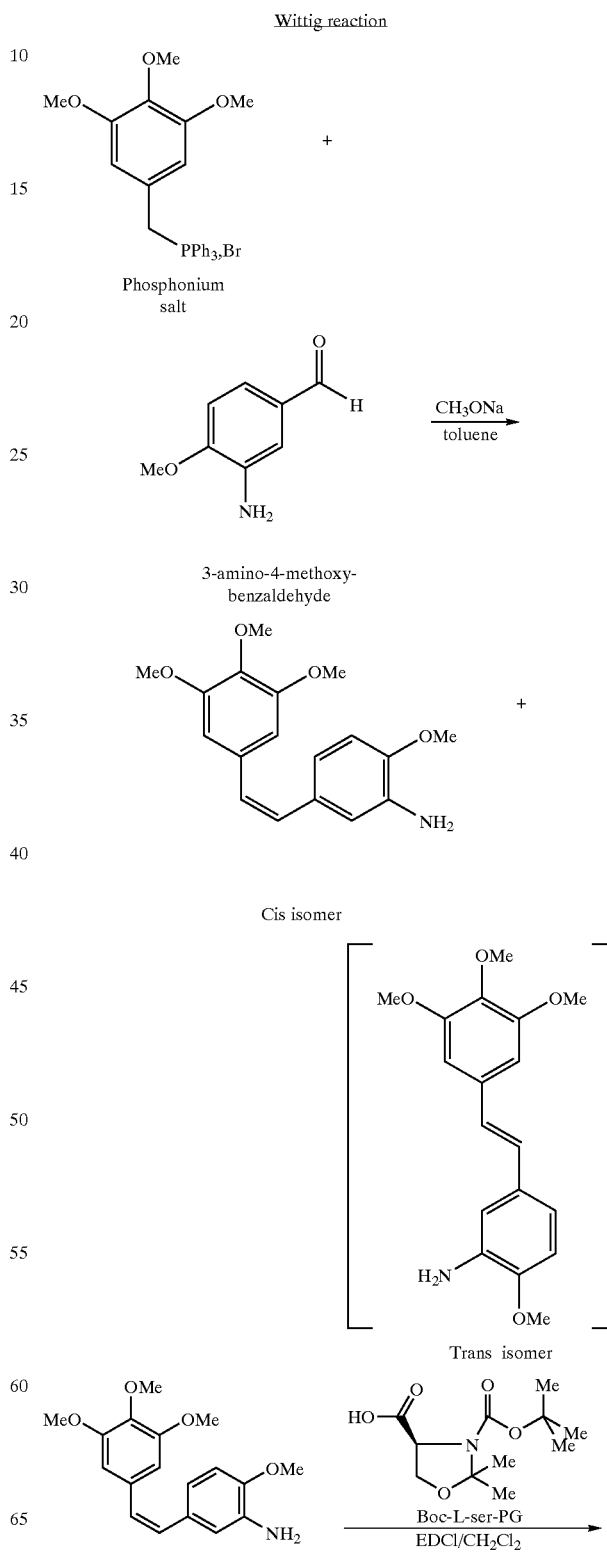

-continued

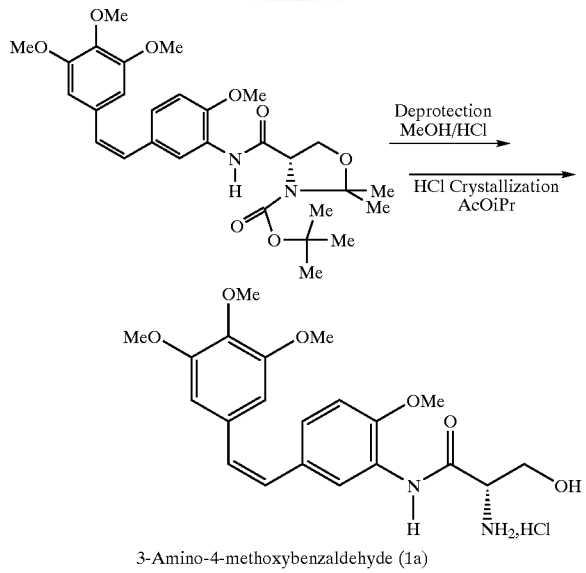

3-Amino-4-methoxybenzaldehyde (1a)

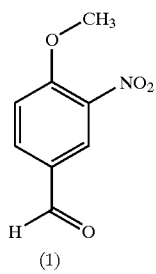  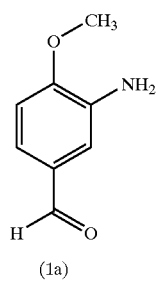

3-Nitro-4-methoxybenzaldehyde (1, 20 g) and 350 ml of absolute ethanol are charged into a 2 litre three-necked flask under argon and equipped with a mechanical stirrer, a thermometer, a T piece, a funnel for the addition of solids, a reflux condenser surmounted by a bubble counter, and a heating bath. The mixture is stirred and heated to 60° C. to afford a solution. The dropwise addition of 115 ml of distilled water is carried out at 60° C., and followed by addition of 14 ml of 2N hydrochloric acid. Iron powder (24.7 g) is then introduced portionwise. The temperature of the mixture is allowed to return to ambient temperature over 2 hours. The reaction is complete (TLC). The mixture is filtered through CELITE (Celite Corporation, 137 West Central Avenue, Lompoc, Calif. 93436) and concentrated under vacuum. The residue is dissolved in dichloromethane, the organic solution is washed twice with distilled water and then dried over magnesium sulphate, filtered and concentrated to dryness under vacuum. Crude (1a) (16 g) is obtained and is chromatographed on a silica column eluting with dichloromethane. Two fractions comprising the clean expected product are obtained, which fractions, after concentrating, give 11.5 g of pure (1a), i.e. a yield of 69%.

$^1$H N.M.R. spectrum: (300 MHz, $(CD_3)_2SO$, δ in ppm): 3.88 (s, 3H), 5.11 (unresolved peak, 2H), 7.01 (d, J=8 Hz, 1H), 7.14 (d, J=2 Hz, 1H), 7.18 (d, J=8 Hz, 1H), 9.53 (s, 1H).

| Mass spectrum: m = 151 | | | |
|---|---|---|---|
| EI | m/z = 151 | $M^+$ | base peak |
| | m/z = 136 | $[M-CH_3]^+$ | |

| Mass spectrum: m = 151 | |
|---|---|
| m/z = 108 | $[136-CO]^+$ |
| m/z = 80 | $[108-CO]^+$ |

IR spectrum: KBr 3464, 3437, 3367, 3349, 1675, 1655, 1582, 1513, 1293, 1241, 1139, 1023, 803 and 640 $cm^{-1}$

Z- and E-2-Methoxy-5-[2-(3,4,5-trimethoxyphenyl)vinyl]phenylamine (8') and (9')

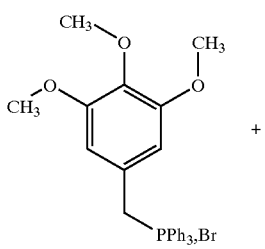

(2a)

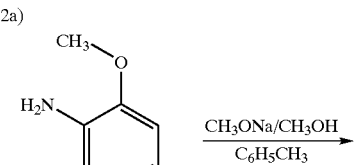

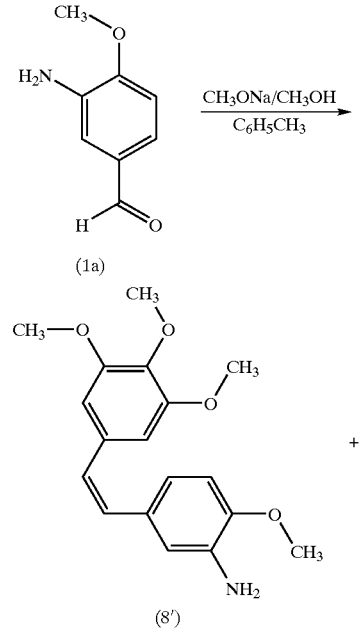

(8')

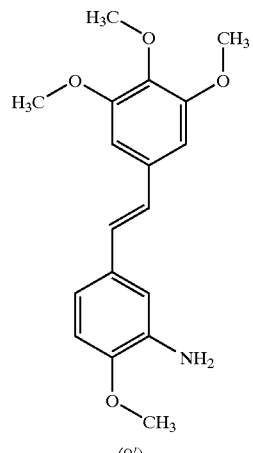

(9')

The phosphonium salt (2a) is a starting material already disclosed in the original patent Ajinomoto Co. Ltd, U.S. Pat. No. 5,525,632 and WO 01/12579 A2.

Phosphonium salt (2a, 8.0 g), followed by 2.20 g of aminobenzaldehyde (1a) and 100 ml of toluene, are charged into a 250 ml three-necked flask under nitrogen and equipped with a magnetic stirrer, a thermometer, a T piece, a dropping funnel, a reflux condenser surmounted by a bubble counter, and a cooling bath. The stirred suspension is cooled to 5° C. and 3.51 ml of a 25% w/w methanolic sodium methoxide solution are added over 15 minutes. After 2.5 hours at 5° C., the reaction remains incomplete (conversion rate: 45%) but does not change further (HPLC) and the Z/E ratio is 61/39. Acetic acid (0.2 ml) diluted in 50 ml of water is then added, the temperature rises to 13° C., the mixture is stirred for 30 minutes and then the phases are separated. The organic phase is concentrated under vacuum on a rotary evaporator and 8 g of a yellow oil are obtained. By HPLC, this oil comprises starting aldehyde, phosphine oxide and the expected product mixture with a Z/E ratio of 61/39. The oil is chromatographed on a silica column (40 parts w/w) eluting with a cyclohexane/ethyl acetate/triethylamine (50/50/2) mixture. Two series of combined fractions are concentrated to dryness: the first dry extract of 360 mg consists of 93% of the Z isomer plus unidentified impurities; the second, of 2.09 g, consists of starting aldehyde and a Z/E mixture representing 39% and 37.5% by IS HPLC. The balance by weight of Z isomer (8'), determined by IS HPLC, is 1.15 g with respect to 2.20 g of aldehyde charge, i.e. a yield of 24%.

EXAMPLE 3

Synthesis According to the Second Process Route V0 3 According to the Invention The advantage of route V0 3 with respect to the first "inverse Wittig" process route V0 2 is that of carrying out the Wittig reaction between a product which has already been reduced, (3-amino-4-methoxybenzyl)triphenylphosphonium bromide (1b), and 3,4,5-trimethoxybenzaldehyde (5) and thus of eliminating a chemical stage which gives off CMR products.

(Z)-N-[2-Methoxy-5-[2-(3,4,5-trimethoxyphenyl)vinyl]phenyl]-L-serinamide hydrochloride General Scheme of the Synthesis Wittig reaction

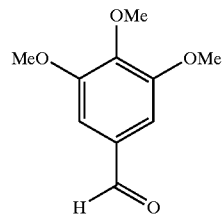

3,4,5-trimethoxy-benzaldehyde

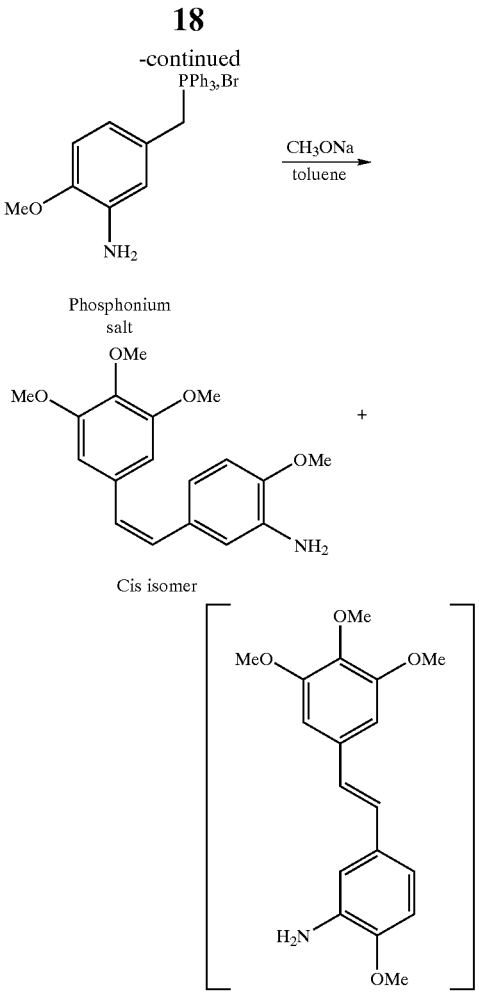

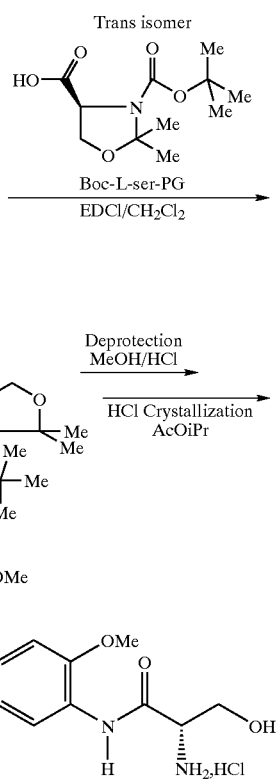

-continued (4-Methoxy-3-aminobenzyl)triphenylphonium bromide (1b)

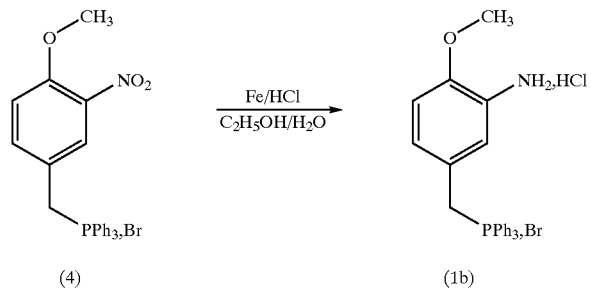

Compound (4, 30 g), 240 ml of ethanol and 60 ml of distilled water are charged into a 1 litre three-necked flask equipped with a mechanical stirrer, a thermometer, a T piece, a funnel for the addition of solid, a reflux condenser surmounted by a bubble counter, and a heating bath. 6N hydrochloric acid (1.76 ml) is added to the stirred suspension, which is heated to 70° C. Iron powder (9.9 g) is then added portionwise over 15 minutes; the mixture remains insoluble. The mixture is maintained at 75° C. for 2 hours; the organic materials slowly pass into solution while a brownish deposit of iron and of iron oxide is formed. After monitoring by HPLC, 5% of starting material still remains; 2 g of iron are again added and heating is continued for 1 hour; the conversion is complete. The mixture is cooled to 40° C. and filtered through clarcel, the filter residue is rinsed with 100 ml of ethanol containing 20% water, and the filtrate is concentrated to dryness under vacuum on a rotary evaporator. The residue is taken up in 300 ml of isopropanol and crystallizes from the mixture, which on stirring and heating to 50° C. passes back into solution. A 5N solution of hydrochloric acid in isopropanol (14 ml) are then added, a precipitate forms, the mixture is held at 50° C. for 1 hour and then it is allowed to return to ambient temperature. The slurry is filtered through a sintered glass filter and the filter cake is washed with 50 ml of isopropanol, sucked dry thoroughly and dried in an oven under vacuum. Compound (1b, 27.3 g) is obtained with a yield as such of 89.9%.

$^1$H N.M.R. spectrum: (300 MHz, $(CD_3)_2SO$, δ in ppm): 3.78 (s, 3H), 5.03 (broad d, J=15 Hz, 2H), 6.43 (unresolved peak, 1H), 6.62 (broad s, 1H), 6.82 (broad d, J=8 Hz, 1H), from 7.60 to 8.00 (mt, 15H).

| Mass spectrum: m = 397 | | | |
|---|---|---|---|
| EI | m/z = 397 | M$^+$ | |
| | m/z = 382 | [M—CH$_3$]$^+$ | |
| | m/z = 262 | [PPh$_3$]$^+$ | base peak |
| DCI | m/z = 398 | MNH$_4$$^+$ | |
| | m/z = 263 | [PPh$_3$H]$^+$ | base peak |

IR spectrum: KBr 3254, 2474, 1920, 1628, 1520, 1439, 1433, 1279, 1110, 736, 690, 527 and 511 cm$^{-1}$ Z- and E-2-Methoxy-5-[2-(3,4,5-trimethoxyphenyl)vinyl]phenylamine (8') and (9')

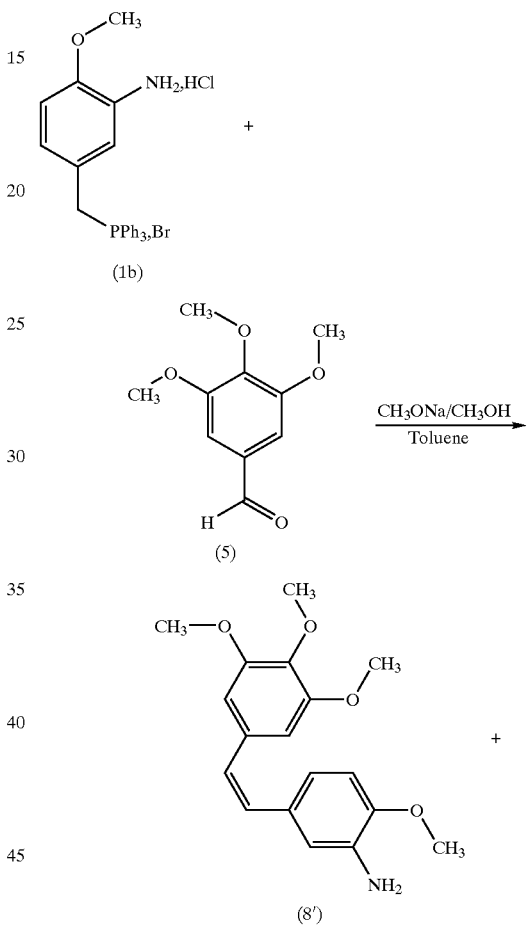

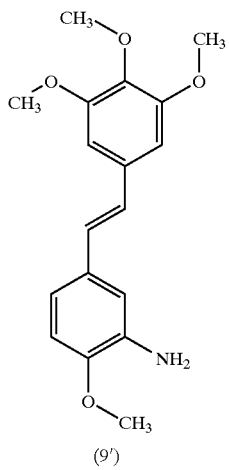

Compound (1b, 11.02 g), 4 g of (5) and 70 ml of toluene are charged into a 250 ml three-necked flask under nitrogen and equipped with a magnetic stirrer, a thermometer, a T piece, a dropping funnel, a reflux condenser surmounted by a bubble counter, and a cooling bath. The stirred suspension is cooled to 5° C. and 4.92 ml of a 25% w/w solution of sodium methoxide in methanol are added over 15 minutes. The suspension is stirred at 5° C. for 2.5 hours, then 0.2 ml of acetic acid diluted in 50 ml of water is added, the temperature rises to 14° C. and the mixture becomes very thick. It is diluted with 10 ml of toluene and 10 ml of water. A brown insoluble material remains. The mixture is filtered through clarcel, the filter cake is washed 3 times with 50 ml portions of toluene (the wash liquors comprise virtually only the starting aldehyde and are not added to the two-phase filtrate), the phases of the clear filtrate (pH 12) are separated, and the organic phase is concentrated to dryness under vacuum at 40° C. The Z/E ratio, determined by IS HPLC, is 43/57. The resultant brown oil (4 g) is chromatographed on a silica column (100 parts w/w) eluting with a cyclohexane/ethyl acetate/triethylamine (50/50/2) mixture. Two series of combined fractions are concentrated to dryness: the first dry extract of 1.1 g consists of 14% of E isomer and 59% of Z isomer; the second weighs 1.08 g and consists of 86% of E isomer and 7% of Z isomer. The balance by weight of Z isomer (8'), determined by IS HPLC, is 0.725 g with respect to 4 g of aldehyde charged, i.e., a yield as such of 11.3%.

Z-4-{2-Methoxy-5-[2-(3,4,5-trimethoxyphenyl)vinyl]phenylcarbamoyl}-2,2-dimethyloxazolidine-3-carboxylic acid tert-butyl ester (11)

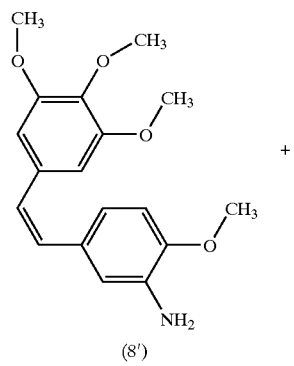

+

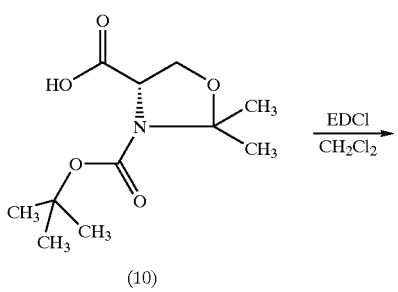

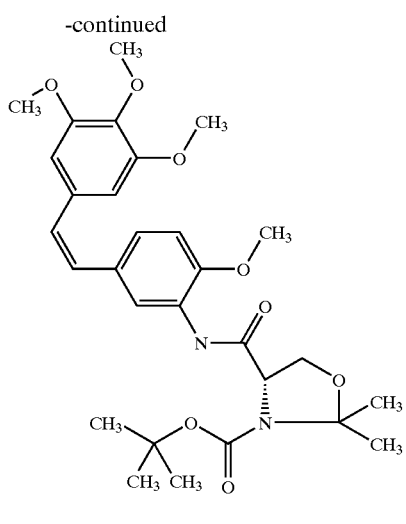

(11)

Release of the Base (8') from the Hydrochloride (8)

Compound (8) (44 g), 16 g of sodium hydrogen carbonate and then 200 ml of distilled water and 375 ml of dichloromethane are charged into a 1 litre Erlenmeyer flask. The mixture is stirred for 20 minutes at ambient temperature and two clear phases are obtained. The organic phase is separated, dried over sodium sulphate and then filtered. Approximately 400 ml of a dichloromethane solution comprising (8') are obtained.

Preparation of 2,2-dimethyloxazolidine-3,4-dicarboxylic acid 3-tert-butyl ester (10)

Although commercially available, this product is very difficult to obtain. The compound was therefore prepared by saponification with lithium hydroxide of its methyl ester according to: J. Org. Chem., 63(12), p. 3983 (1998).

$^1$H N.M.R. spectrum:(300 MHz, $(CD_3)_2SO$, δ in ppm): 1.38 (s, 3H), 1.45 (s, 9H), 1.55 (s, 3H), 3.95 (mt, 1H), 4.16 (mt, 1H), 4.31 (mt, 1H), from 12.50 to 13.10 (broad unresolved peak, 1H).

| Mass spectrum: m = 245 | | | |
|---|---|---|---|
| DCI | m/z = 263 | $MNH_4^+$ | |
| | m/z = 246 | $MH^+$ | |
| | m/z = 207 | $[MNH_4\text{-t-Bu}]^+$ | base peak |
| | m/z = 146 | $[MH\text{-BOC}]^+$ | |

IR spectrum: KBr
1744, 1704, 1638, 1407, 1368, 1164, 1104, 856, 836 and 623 cm$^{-1}$ Coupling The solution of (8') is charged into a 2 litre three-necked flask equipped with a mechanical stirrer, a thermometer, a T piece, a funnel for the addition of solid, a reflux condenser surmounted by a bubble counter, and an ice bath, 600 ml of dichloromethane are added and the mixture is cooled with stirring. 2,2-Dimethyloxazolidine-3,4-dicarboxylic acid 3-tert-butyl ester (10, 42.9 g) is added at 5° C., a solution forms, and then 48 g of 1-(3-dimethylaminopropyl)-3-ethylcarbodiimide hydrochloride (EDCI) are added portionwise between 5° C. and 10° C. The mixture is slowly allowed to return to ambient temperature by allowing the ice in the bath to melt overnight. In the morning, 330 ml of distilled water are added and the mixture is vigorously stirred. The mixture turns cloudy over 30 minutes (hydrolysis of the EDCI). Stirring is maintained for a further 30 minutes. The mixture is separated by settling in a separating funnel and the organic phase is washed successively twice with 280 ml portions of 0.55N sodium hydroxide solution and then with 300 ml of distilled water. The organic phase is concentrated to dryness on a rotary evaporator (50° C./50 mmHg). A sticky oil (79.4 g, 11) is obtained, which oil hardens at 20° C., with a yield by weight with respect to (8) charged of 117%.

$^1$H N.M.R. spectrum: (400 MHz, $(CD_3)_2SO$, at a temperature of 373 K, δ in ppm): 1.41 (s, 9H), 1.53 (s, 3H), 1.64 (s, 3H), 3.64 (s, 6H), 3.71 (s, 3H), 3.86 (s, 3H), 3.99 (dd, J=9 and 3 Hz, 1H), 4.19 (dd, J=9 and 7 Hz, 1H), 4.52 (dd, J=7 and 3 Hz, 1H), 6.48 (d, J=12.5 Hz, 1H), 6.55 (d, J=12.5 Hz, 1H), 6.58 (s, 2H), 7.02 (mt, 2H), 8.13 (broad s, 1H), 8.82 (broad s, 1H).

| Mass spectrum: m = 542 | | | |
| --- | --- | --- | --- |
| DCI | m/z = 560 | $MNH_4^+$ | base peak |
|  | m/z = 543 | $MH^+$ |  |
|  | m/z = 504 | $[MNH_4\text{-t-Bu}]^+$ |  |
|  | m/z = 443 | $[MH\text{-BOC}]^+$ |  |

IR spectrum: $CCl_4$ 3409, 2982, 2938, 2837, 1712, 1698, 1534, 1363, 1249, 1133, 1092 and 851 $cm^{-1}$ Other coupling conditions were employed, such as:

Mixed anhydride (pivaloyl chloride/(10)).
DCC/HOBT, DCC/HOSU, TOTU, N,N-carbonyldiimidazole, and the like.
In acetonitrile, DMF, THF, dichloromethane, ester, and the like.
EDCI HCl in dichloromethane gave the best result.

(Z)-N-[2-Methoxy-5-[2-(3,4,5-trimethoxyphenyl)vinyl]phenyl]-L-serinamide hydrochloride

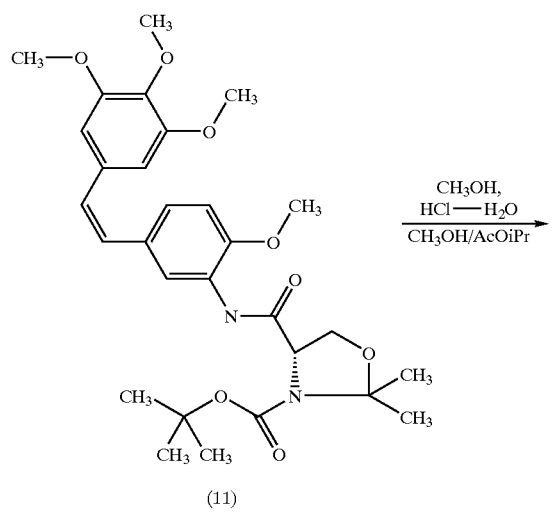

(11)

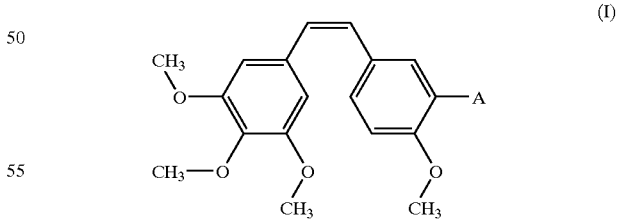

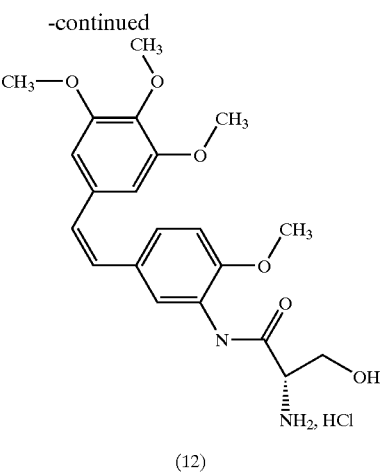

(12)

Compound (11) (61.8 g), dissolved in 54 ml of methanol, is charged at 20° C. into a 1 litre three-necked flask equipped with a mechanical stirrer, a thermometer, a T piece, a reflux condenser surmounted by a bubble counter, and a heating bath, and 150 ml of isopropyl acetate, 99 ml of a 2.3N solution of hydrochloric acid in methanol and 8.2 ml of distilled water are added. The mixture is stirred and heated at 60° C. for 3 hours. The solution, cooled to 40° C., is clarified by filtration through a sintered glass filter (No. 4) rinsed with 40 ml of methanol. The filtrate is returned to the stirred three-necked flask, 194 ml of isopropyl acetate are added, the mixture is reheated to 40° C., the solution is seeded with 0.2 g of (12) and then 194 ml of isopropyl acetate are added dropwise over 1 hour. The mixture slowly crystallizes as the isopropyl acetate is being added. The mixture is allowed to return to ambient temperature and is then cooled to and maintained overnight at 5° C. In the morning, the slurry is filtered through a sintered glass filter and the filter cake is sucked dry, washed four times with 50 ml portions of isopropyl acetate, sucked thoroughly dry and then dried in an oven to constant weight (35° C./10 mmHg). Compound (12) (28 g) is obtained with a yield over 2 stages (coupling and then deprotection operations) of: 56%, and an IS HPLC assay >98%, i.e. an overall yield as such, for the synthesis carried out according to the first process route V0 2, of 30% [(12) obtained with respect to (5) charged].

What is claimed is:

1. A process for the preparation of a compound of formula (I)

(I)

wherein A is $NH_2$,
comprising the steps of:
 a. condensing a (3,4,5-trimethoxybenzyl)triphenylphosphonium salt and 3-nitro-4-methoxybenzaldehyde; or
 b. condensing 3,4,5-trimethoxybenzaldehyde and a (4-methoxy-3-nitrobenzyl)triphenylphosphonium salt to provide a nitro intermediate of formula (I) wherein A is $NO_2$; and c. reducing the nitro intermediate with iron powder to provide a compound of formula I wherein A is NH$_2$, and d. optionally converting the compound of formula (I) wherein A is NH$_2$ to a pharmaceutically acceptable salt thereof.

2. The process of claim 1 wherein iron powder is used in an amount greater than about two equivalents of iron powder per one mole of the nitro intermediate.

3. The process of claim 2 wherein iron powder is used in an amount from about two equivalents to about four equivalents.

4. A process for the preparation of a compound of formula (I)

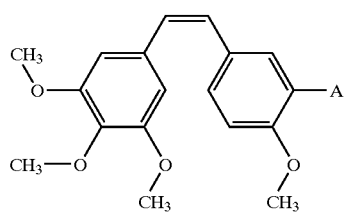
(I)

wherein A is NH$_2$, comprising the step of:

a. condensing a (3,4,5-trimethoxybenzyl) triphenylphosphonium salt and 3-amino-4-methoxybenzaldehyde in a suitable solvent at a suitable temperature in the presence of a base to provide a compound of formula (I) wherein A is NH$_2$, or b. condensing 3,4,5-trimethoxybenzaldehyde and a (3-amino-4-methoxybenzyl)triphenylphosphonium salt in a suitable solvent at a suitable temperature in the presence of a base to provide a compound of formula (I) wherein A is NH$_2$, and c. optionally converting the compound of formula (I) wherein A is NH$_2$ to a pharmaceutically acceptable salt thereof.

5. The process according to claim 4 wherein the (3,4,5-trimethoxybenzyl)-triphenylphosphonium salt is condensed with 3-amino-4-methoxybenzaldehyde.

6. The process according to claim 4 wherein the solvent is selected from the group consisting of THF, acetonitrile, NMP, DMF, DMSO and toluene.

7. The process according to claim 4 wherein the base is selected from the group consisting of potassium tert-butoxide, sodium tert-pentoxide, sodium hydride, butyllithium, lithium diisopropylamide, sodium methoxide, potassium carbonate and alkaline derivatives of hexamethyldisilazane.

8. The process according to claim 7 wherein the base is sodium methoxide.

9. The process according to claim 8 wherein the temperature is from about 0° C. to about 10° C.

10. A process for the preparation of a compound of formula (I)

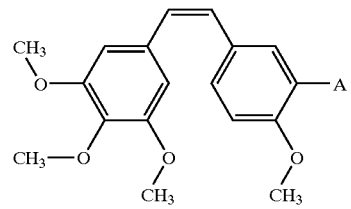
(I)

wherein A is

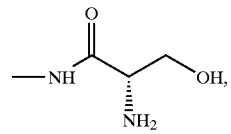

comprising the steps of:

a. condensing a compound of formula (I) wherein A is NH$_2$ and a doubly protected L-serine of formula (IIb)

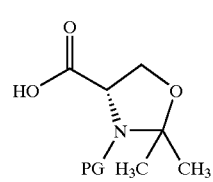
(IIb)

wherein PG is a protecting group selected from the group consisting of tert-butoxycarbonyl, benzyloxycarbonyl and 9-fluorenylmethyloxycarbonyl, in a suitable solvent and in the presence of a suitable condensing agent to provide a compound of formula (III)

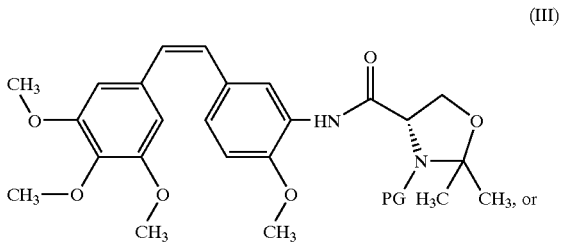
(III)

b. condensing a compound of formula (I) wherein A is NH$_2$ and a mixed anhydride which is prepared from a chloroformate or a carboxylic acid chloride and a doubly protected L-serine of formula (IIb) to provide a compound of formula (III), and c. hydrolyzing the compound of formula (III) at a suitable temperature to provide a compound of formula I wherein A is

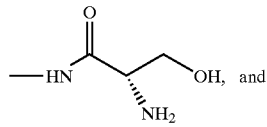
and d. optionally converting the compound of formula (I) wherein A is

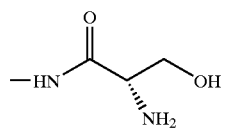

to a pharmaceutically acceptable salt thereof.

11. The process according to claim 10 wherein the condensing agent is selected from the group consisting of 1-(3-dimethylaminopropyl)-3-ethylcarbodiimide hydrochloride, O-benzotriazol-1-yl-N,N,N',N'-tetramethyluronium hexafluorophosphate, N,N-carbonyldiimidazole, a mixture of dicyclohexylcarbodiimide and hydroxybenzotriazole, and a mixture of dicyclohexylcarbodiimide and N-hydroxysuccinimide.

12. The process according to claim 11 wherein the solvent is selected from the group consisting of acetonitrile, DMF, THF and dichloromethane.

13. The process according to claim 12 wherein the solvent is dichloromethane.

14. The process according to claim 13 wherein the condensing agent is 1-(3-dimethylaminopropyl)-3-ethylcarbodiimide hydrochloride.

15. The process of claim 10 wherein the mixed anhydride is prepared by treating the compound of formula (IIb) with pivaloyl chloride.

16. The process according to claim 10 wherein the hydrolysis is conducted under acidic conditions.

17. The process according to claim 16 wherein the acid is concentrated aqueous hydrochloric acid in an alcoholic medium.

18. The process according to claim 17 wherein the alcoholic medium is methanol.

19. The process according to claim 18 wherein the temperature is from about 50° C. to about 70° C.

20. A compound of formula (III)

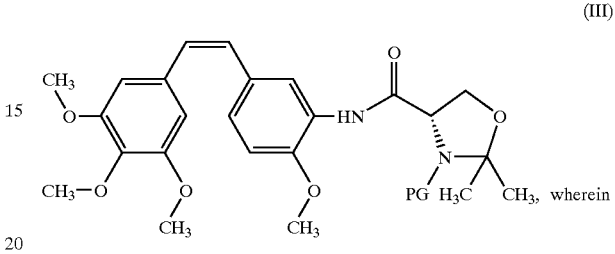

wherein
PG is selected from the group consisting of tert-butoxycarbonyl, benzyloxycarbonyl and 9-fluorenylmethyloxycarbonyl.

* * * * *